US005629009A

United States Patent [19]

Laurencin et al.

[11] Patent Number: 5,629,009
[45] Date of Patent: May 13, 1997

[54] DELIVERY SYSTEM FOR CONTROLLED RELEASE OF BIOACTIVE FACTORS

[75] Inventors: Cato T. Laurencin, Somerville, Mass.; Paul A. Lucas, Macon, Ga.; Glenn T. Syftestad, Sacramento, Calif.; Abraham Domb, Baltimore, Md.; Julie Glowacki, Jamaica Plan; Robert S. Langer, Newton, both of Mass.

[73] Assignee: Massachusetts Institute of Technology, Cambridge, Mass.

[21] Appl. No.: 693,466

[22] Filed: Aug. 7, 1996

Related U.S. Application Data

[62] Division of Ser. No. 222,880, Apr. 5, 1994, Pat. No. 5,545,409, which is a continuation of Ser. No. 59,516, May 7, 1993, Pat. No. 5,356,630, which is a continuation of Ser. No. 742,264, Aug. 7, 1991, abandoned, which is a continuation of Ser. No. 313,953, Feb. 22, 1989, abandoned.

[51] Int. Cl.$^6$ .................. A61F 2/28; A61K 38/39; C07K 14/485; C07K 14/51
[52] U.S. Cl. .................. 424/426; 514/2; 514/21; 530/300; 530/353; 530/840; 623/14
[58] Field of Search .................. 424/426, 423; 514/2, 21; 530/300, 353, 840; 623/14

[56] References Cited

U.S. PATENT DOCUMENTS

| | | | |
|---|---|---|---|
| 2,071,250 | 2/1937 | Carothers | 526/71 |
| 2,071,251 | 2/1937 | Curothers | 524/31 |
| 2,073,799 | 3/1937 | Hill | 554/122 |
| 2,621,145 | 12/1952 | Sano | 424/423 |
| 2,668,182 | 2/1954 | Lowe | 528/357 |
| 2,676,945 | 4/1954 | Higgins | 524/710 |
| 2,958,678 | 11/1960 | Conix | 528/86 |
| 2,960,493 | 11/1960 | Conix | 528/206 |
| 3,526,612 | 9/1970 | Allphln | 528/363 |
| 3,625,214 | 12/1971 | Higuchi | 424/424 |
| 3,766,145 | 10/1973 | Thompson | 528/366 |
| 3,811,444 | 5/1974 | Haller et al. | 424/428 |
| 3,887,699 | 6/1975 | Yolles | 424/477 |
| 3,914,401 | 10/1975 | Sharabash | 424/462 |
| 3,960,150 | 6/1976 | Hussain et al. | 424/428 |
| 3,978,071 | 8/1976 | Sadek | 424/425 |
| 3,981,303 | 9/1976 | Higuchi et al. | 424/428 |
| 3,986,510 | 10/1976 | Higuchi et al. | 424/428 |
| 3,991,766 | 11/1976 | Sohmitt et al. | 606/230 |
| 3,993,071 | 11/1976 | Highuchi et al. | 424/428 |
| 4,014,987 | 3/1977 | Heller et al. | 424/486 |
| 4,036,227 | 7/1977 | Zaffaroni et al. | 424/428 |
| 4,070,347 | 1/1978 | Schmitt | 528/271 |
| 4,096,238 | 6/1978 | Zaffaroni et al. | 424/467 |
| 4,394,370 | 7/1983 | Jefferies | 424/15 |
| 4,419,340 | 12/1983 | Yolles | 514/33 |
| 4,489,056 | 12/1984 | Himmelstein et al. | 424/486 |
| 4,563,489 | 1/1986 | Urist | 514/21 |
| 4,609,551 | 9/1986 | Caplan et al. | 514/2 |
| 4,610,692 | 9/1986 | Eitenmuller et al. | 424/423 |
| 4,612,009 | 9/1986 | Drobnik et al. | 424/426 |
| 4,637,931 | 1/1987 | Schmitz | 424/426 |
| 4,675,189 | 6/1987 | Kent et al. | 424/490 |
| 4,757,128 | 7/1988 | Domb et al. | 528/271 |
| 4,789,724 | 12/1988 | Domb et al. | 528/176 |
| 4,797,282 | 1/1989 | Wahlig et al. | 424/422 |
| 4,806,621 | 2/1989 | Kohn et al. | 528/221 |
| 4,832,686 | 5/1989 | Anderson | 604/49 |
| 4,886,870 | 12/1989 | D'Amore et al. | 524/599 |
| 4,888,176 | 12/1989 | Langer et al. | 514/772.3 |
| 4,891,225 | 1/1990 | Langer et al. | 524/599 |
| 4,906,474 | 3/1990 | Langer et al. | 514/772.3 |
| 4,961,707 | 10/1990 | Magnusson et al. | 424/426 |
| 4,975,528 | 12/1990 | Kuberasampath et al. | 530/350 |
| 5,013,553 | 5/1991 | Southard et al. | 424/426 |
| 5,122,367 | 6/1992 | Ron et al. | 514/2 |
| 5,286,763 | 2/1994 | Gerhart et al. | 514/772.4 |

FOREIGN PATENT DOCUMENTS

| | | |
|---|---|---|
| 684685 | 4/1964 | Canada . |
| 2690262 | 5/1987 | France . |
| 60-141725 | 7/1985 | Japan . |
| 838986 | 6/1960 | United Kingdom . |
| 840846 | 7/1960 | United Kingdom . |
| 840847 | 7/1960 | United Kingdom . |
| 968715 | 9/1964 | United Kingdom . |
| WO89/00855 | 2/1989 | WIPO . |

OTHER PUBLICATIONS

Polyanhydridas *Encyclopedia of Polymer Science & Technology* (John Wiley & Sons New York 1969) vol. 10, pp. 630–653.

Bayston and Milner, "The Sustained Release Of Antimicrobial Drugs From Bone Cement", *J. Bone Joint Surg.* 64–B(4);460–464 (1982).

Bucher and Slade, "The Anhydrides of Isophthalio And Terephtalic Acids", *J. Amer. Chem. Soc.* 37:1319–1325 (1909).

Buchholz and Engelbracht "Uber die Depotwirkung einger bie Vermischung mit Kunstbarz Balacos", *Der Chizurg* 41:511–514 (1970).

Buchholz et al., "Antibiotic–loaded Acrylic Cement: Current Concepts", *Clin. Orthop.* 180:96–108 (1984).

Cawley et al., "Sustained release of a corricosteroid using polymeric implants", Agents and Actions 19(3/4):233–243 (1986).

Conix *Macromolecular Synthases* vol. 2 (John Wiley & Sons New York 1966) pp. 95–99.

Cottler and Matzner, "Polyanhybrides Een overzicht van bareidingswilzen en aigenschannen", Chemisch Weekblad 63:113–126 (1967).

(List continued on next page.)

Primary Examiner—Carlos Azpuru
Attorney, Agent, or Firm—Arnall Golden & Gregory

[57] ABSTRACT

A composition and method for controlled release of water-soluble proteins comprising a surface-eroding polymer matrix and water-soluble bioactive factors is described. The composition bioerodes in the biological environment of the subject at a controlled rate, thereby releasing the water soluble proteins at a rate which allows them to interact with local cell populations.

9 Claims, No Drawings

OTHER PUBLICATIONS

Deatharage et al., "Packaging and Delivery of Bone Induction Factors in a Collagenous Implant", Collagen and Related Research, 7:225–231 (1987).

Gerhart et al., "Antibiotic Release From an Experimental Biodegradable Bone Cement" *J. Orthop. Res.* 6:585–592 (1988).

Hill and Carothers, "Studies Of Polymerization And Ring Formation. XIV, A Linear Superpolyanhydride And A Cyclic Dimetric Anhydrids From Sebecic Acid", *J. Amer. Chem. Soc.* 54:1569–1579 (1932).

Hill and Carothers, "Studies of Polymerization and Ring Formation XIX Manv–Membered Cyclic Anhydrides", *J. Amer. Chem. Soc.* 55:5023–5031 (1933).

Lang et al., "Bioerodible polyanhydrides as drug–carrier matrices I: Characterization degradation and release characteristics", *Journal of Biomedical Materials Research.* 19:941–955 (1985).

Leong et al., "Bioerodible polyanhydrides as drug–carriers matrices, II, Biocompatibility and chemical reactivity", Journal of *Biomedical Materials Research,* 20:51–64 (1986).

Leong et al., "Synthesis of Polyanhydrides: Melt–Polycondensation, Dehydrochlorination, and Dehydrative Coupling", *Macromolecules* 20(4):705–712 (1987).

Lucas et al., "A water–soluble fraction from adult bone stimulates the differentiation of cartilage in explants of embryonic muscle", *Differentiation,* 37:47–52 (1988).

Lucas et al., "Ectopic induction of cartilage and bone by water–soluble proteins from bovine bone using a collagenous delivery vehicle", *Journal of Biomedical Materials Research,* 23:23–39 (1989).

Mockey et al., "Antibiotic Loaded Plaster of Paris Pellets: An In vitro Study of a Possible Method of Local Antibiotic Therapy in Bone Infection", *Clin. Orthop.* 167:263–268 (1982).

Maiid et al., "Gentamicin–PMMA beads in the treatment of Chronic ostcomyalitis", *Acta. Ortho. Scand.* 56:265–268 (1985).

McLaran and Miniaci, "In Vivo Study To Determine The Efficacy Of Cancellous Bone Graft As A Delivery Vehicle For Antibiotics", *Transactions of the 12th Annual Meeting of the Society for Biomaterials,* Abstract 102, May 29 to Jun. 1, 1986.

Nathan et al "Osteogenesis in Rats With an Inductive Bone Composite", *Journal of Orthopedic Research,* 6:324–331 (1988).

Reddi and Huggins, "Biochemical Sequences in the Transformation of Normal Fibroblasts in Adolescent Rats", *Proceedings of the National Academy of Science, USA,* 69:1601–1605 (1972).

Rossen et al "Bioerodible poyanhydrides for controlled drug delivery", *Biomaterials* 4:131–133 (1983).

Sampath et al., "Isolation of osteogenin on extracellular matrix–associated bone–inductive protein by heparin affinity chromatography", *Proceedings of the National Academy of Sciences, USA,* 84:7109–7113 (1987).

Syftestad and Caplan "A Fraction from Extracts of Domineralized Adult Bone Stimulates the Conversin of Messenchymol Cells into Chondrocytes", *Developmental Biology,* 104:348–356 (1984).

Syftastad et al., "The in vitro chondrogenic response of limb–bud mesenchyme to a water–soluble fraction prepared from demineralized bone matrix", *Differentiation,* 29:230–237 (1985).

Trippel "Antibiotic–Impregnated Cement in Total Joint Arthroplasty", *J. Bone Joint Surg.* 68–A(8):1297–1302 (1986).

Ursit "Bone:Formation by Autoinduction", *Science,* 150:893–899 (1965).

Urist et al., "Purification of bovine bone morphogenic protein by hydroxvapatite chromatography", *Proceedings of the National Academy of Sciences, USA,* 81:371–375 (1984).

Vecsei and Berguet, "Treatment of Chronic Osteomyalitis by Necrectomy and Gentamicin–PMMA Beads", *Clin. Orthop.* 159:201–207 (1981).

Wang et al., "Purification and characterization of other distinct bone–inducing factors", *Proceedings of the National Academy of Sciences, USA,* 85:9498–9488 (1988).

Yoda "Synthesis of Polyanhydride I Mixed Anhydride of Aromatic and Aliphatic Dibasic Acids", *Bull. Chem. Soc. Japan*32(10):1120–1126 (1959).

Yoda "Syntheses of Polyanhydrides XII Crystalline and High Melting Polyamidepolyanhydrides of Methylenebis carboxyphenyl amide", *J. Polymer Science: Part A* 1:1323–1338 (1963).

Yoda, "Synthesis of Polyanhydrides II New Polyanhydrides with High Melting Points and Fiber–Forming Properites", *Makromolokulere Chemie*32:1–12 (1969).

Yoda "Synthesis of Polyanhydrides III Polyanhydrides of Five–membered Heterocyclic Dibasic Acids", *Makromolekulere Chemie* 55:174–190 (1962).

Yoda "Synthesis of Polyanhydrides X Mixed Anhydrides of Aromatic and Five–membered Heterocyclic Diabasic Acids", *Makromolekulere Chemie* 56:10–35 (1962).

Yoda "Synthesis of Polyanhydrides" *Makromolekulere Chemie* 56:36–54 (1962).

DELIVERY SYSTEM FOR CONTROLLED RELEASE OF BIOACTIVE FACTORS

GOVERNMENT FUNDING

The work described herein has been funded by a grant from the National Institutes of Health.

This application is a Divisional of Ser. No. 08/222,880, filed Apr. 5, 1994, now U.S. Pat. No. 5,545,409 which is a continuation of Ser. No. 08/059,516, filed on May 7, 1993, now U.S. Pat. No. 5,356,630, which is a continuation of U.S. Ser. No. 07/742,264, filed Aug. 7, 1991, now abandoned, which is a continuation of U.S. Ser. No. 07/313,953, filed Feb. 22, 1989, now abandoned.

BACKGROUND

The sustained administration of drugs over an extended period of time has significant medical and practical advantages in clinical practice. In recent years, much research has been done in developing systems for the sustained release of biologically active substances, particularly drugs, over periods of time. The purpose of these systems is to dispense the drug or other substance in a controlled manner at a selected physiological site. In the case of drugs used for therapy, presenting the drug in the most efficacious manner to effect treatment is desirable, while simultaneously minimizing complications which may occur as a result of the drug delivery.

Presently available systems for the sustained release of drugs are generally polymeric compositions where the drug or agent is either an integral part of the polymer matrix or layered or contained as a discrete portion of the device. For example, Folkman and Langer in U.S. Pat. No. 4,291,797 describe a delivery device for macromolecules in which the macromolecule is interspersed throughout the polymer matrix.

In U.S. Pat. No. 4,767,628, Hutchinson describes a delivery vehicle formed of polylactide polymer and an acid stable polypeptide interspersed in the matrix.

Higuchi in U.S. Pat. No. 3,625,214 describes a sustained release drug delivery device according to a defined release profile by layering the drug and a bioerodible polymer.

Michaels in U.S. Pat. No. 3,867,519 describes a sustained drug delivery device wherein release of the drug is controlled by the composition of an anionic polyvalent metal cation cross-linked polyelectrolyte.

In U.S. Pat. No. 4,093,709 Choi and Heller describe a controlled release device formed from orthoester and orthocarbonate polymers.

While the above systems are useful, they are not appropriate for some applications, such as delivering water-soluble bioactive factors which react with a local cell population at a physiological site. A need exists for systems that can successfully deliver these agents which have favorable release kinetics and allow soluble agents to interact with local cells.

SUMMARY OF THE INVENTION

The invention relates to a composition and method for the controlled administration of a bioactive substance to a local cell population in a subject. The composition comprises a bioerodible, surface-eroding polymer having the bioactive substance interspersed throughout the matrix, which erodes in the biological environment, releasing the bioactive substance to the selected area. The invention also includes a method for delivering water-soluble local-acting substances, particularly proteins, to a specific site in the body of an animal.

The composition and method of the invention allows water-soluble proteins to interact with local cell populations. These proteins are soluble in the physiological environment, and are generally ineffective when introduced in vivo into a biological site because they quickly become diluted and dispersed in the body. The present composition releases soluble proteins directly to a selected site in a concentration sufficient to permit the proteins to interact with the local cell population. The surface-eroding polymers used in the present composition are biocompatible and bioerode in the physiological environment, allowing heterogeneous degradation from the surface of the device, which leads to near zero-order release kinetics. The degradation products of the surface-eroding polymers are non-mutagenic, non-cytotoxic and have a low teratogenic potential.

DETAILED DESCRIPTION OF THE INVENTION

The present invention provides a system for the controlled or sustained release of bioactive substances which interact with local cell populations at a physiological site. The composition is formed from a bioerodible, surface-eroding polymer and the bioactive substance. The "sustained" or "controlled" release of the substance may be either continuous or discontinuous.

The composition of the present invention comprises a bioerodible polymer matrix and a bioactive substance incorporated therein which, when placed in an aqueous physiological environment, releases the bioactive substance in a continuous manner until essentially all of the substance has been released, and the polymer has eroded away. The term "matrix" as used herein denotes a carrier, polymeric phase for the interspersed bioactive substance, which bioerodes in the environment of use, releasing the bioactive substance.

Bioerodible polymers suitable for use in the present invention are polymers which break down or disintegrate over a prolonged period of time when placed in contact with biological fluids. Surface-eroding bioerodible polymers are preferred for use in the present composition. Surface-eroding polymers are, generally, polymers having hydrophobic backbones and hydrolyric linkages, which bioerode from the surface at a constant raze in a biological environment. Surface eroding polymers include polyanhydrides and polyorthoesters.

Polyanhydride polymers are particularly useful for the present compositions. Polyanhydride polymers have several properties which are desirable in a biodegradable, polymeric controlled-release system. These polymers have a hydrophobic backbone and a water labile linkage, which allows heterogeneous degradation in vivo from the surface of the polymer, leading to near zero-order release kinetics. The water-labile anhydride linkage provides the basis for the use of a variety of backbones, each having a unique degradation rate. Thus, the rate of degradation in vivo can be controlled by controlling the length and composition of the polymer backbone. Examples of polyanhydrides which can be used in the present invention include poly[bis(p-carboxyphenoxy) propane anhydride] (PCPP) and poly[bis (p-carboxy) methane anhydride] (PCPM). Co-polymers of polyanhydrides with other substances can also be used. For example, a co-polymer of PCPP and sebacic acid (PCPP-SA) has been shown to be an appropriate material to form a delivery device for soluble proteins. The degradation products of the polyanhydrides are non-mutagenic and non-toxic. In vivo toxicity studies have shown that polyanhydrides have excellent local system biocompatibility. The characteristics of polyanhydride drug carriers for systemic drugs is described by Leong et al. Leong et al., *J. Biomed. Mat. Res.*, 19: 941–955 (1985), Leong et al. *J. Biomed. Mat. Res.*, 20: 51–64 (1986).

Polyanhydride delivery vehicles of the present invention can be used to deliver highly soluble bioactive factors or substances which regulate local cellular events. These factors are generally characterized in that in vitro they produce a response in a cell population, but do not produce a response when used directly in vivo. These substances or factors must be in the vicinity of the cells which they act upon to be effective. These factors are generally water-soluble polypeptides or proteins, which, when introduced into a physiological environment in vivo, are soluble in the environment, and so become too diluted to act locally. Bioactive factors having these characteristics include factors involved in wound healing or angiogenesis, such as TGF-beta, EGF, FGF and PDGF, which act upon local cell populations.

The term "water" as used herein (e.g., water-soluble), includes biological fluids, saline and physiologically acceptable buffer.

In one embodiment of the present invention, bioactive factors which promote chondrogenesis and osteogenesis are used. The protein(s) involved in chondrogenesis/osteogenesis interact with the local cells to influence their proliferation and cytodifferentiation. Transmembrane experiments have shown that the bioactive factor(s) responsible for the chondro-osteoinduction are soluble in body fluids. Nogami and Urist, *Calcif. Tissue Res.*, 19: 153–163 (1975); Urist et al., *Arch. Surg.* 112: 612–619 (1977). It has been demonstrated that cold water-soluble proteins from bone matrix extracts will initiate chondrogenesis in in vitro assay systems. Syftestad and Caplan, *Dev. Biol.*, 104: 348–356 (1984); Syftestad et al., *Differentiation*, 29: 230–237 (1985); Lucas et al., *Differentiation*, 37: 47–52 (1987). However, due to their solubility, these protein fractions do not induce osteogenesis in vivo when implanted alone. It has now been shown that when these proteins are properly formatted in a controlled-release vehicle, they are capable of inducing cartilage and bone in vivo.

Osteogenesis is initiated by an interaction between diffusable bone matrix-derived bioactive factor(s) and local ingrowing cell populations. Reddi and Huggins, *Proc. Nat'l. Acad. Sci. USA*, 69: 1601–1605 (1972). These diffusable factors can be extracted from the demineralized matrix. However, these factors are very soluble in physiological solutions and will not initiate osteogenesis when implanted alone into an ectopic site. (Table 1) Demineralized bone matrix may be viewed as a "natural" sustained release vehicle which releases the soluble bioactive factor(s) in an effective manner. The present invention allows the dose and rate of release of bioactive factors exhibited by pieces of demineralized bone matrix to be mimicked.

The chondro/osteogenic water-soluble proteins used in the present embodiment of the invention are a complex mixture of proteins. Although considerable research has been done to isolate the chondro/osteogenic protein from bone matrix, to date no protein has been unequivocally purified to homogeneity. Urist et al., *Proc. Nat'l. Acad. Sci. USA*, 81: 371–375 (1984); Seyedin et al., *Proc. Nat'l. Acad. Sci. USA*, 82: 2267–2271 (1985); Sampath et al., *Proc. Nat'l Acad. Sci. USA*, 84: 7109–7113 (1987); Sen et al., *Development and Diseases of Cartilage and Bone Matrix*, pp. 201–219, A. Sen and T. Thornhill (eds.), Alan R. Liss, Inc., New York (1987); Wang et al., *Proc. Nat'l. Acad. Sci. USA*, 85: 9484–9488 (1988). Ectopic endochondral ossification occurs through a cascade of events which include recruitment of the local responsive cells, proliferation of the cells, and cytodifferentiation. Each of these steps is thought to involve different bioactive factors, i.e., chemoattractants, mitogens, and chondro/osteogenic factor(s). Reddi, *Current Adv. in Skeletogenesis*, pp. 77–86, M. Silberman and H. Slavkin (eds.), Excerpta Medica, Amsterdam (1982). A crude mixture of proteins is more likely to contain all the necessary bioactive factors. The water-soluble proteins have been shown to be unable to induce ectopic osteogenesis when implanted alone, but to support the osteogenic cascade when incorporated into the herein described composition. When a purified chondro/osteogenic protein becomes available, then the polyanhydride polymers may prove an even more useful delivery vehicle.

The composition of the present invention can be used in manufacturing controlled-release delivery vehicles, which can be manufactured by recognized methods for preparing controlled-release vehicles. See, U.S. Pat. No. 4,391,727; U.S. Pat. No. 4,767,628. In one embodiment, the present compositions were formed by mixing the selected anhydride polymer and the bioactive factors. Briefly, the polyanhydride polymers or co-polymers were synthesized by art-recognized techniques. Leong et al., *J. Biomed. Mat. Res.*, 19: 941–955 (1985); Conix, *Macro. Synth.*, 2: 95–98 (1966). The polymers were ground and sieved into a particle size range of from about 90 to about 150 µm. The water-soluble proteins (i.e., bioactive factors) were mixed with the polymer at the desired ratios, by weight. The relative proportions of polymer to protein will vary depending upon the activity of the protein and the end use of the delivery vehicles. Generally, the protein is present in an amount sufficient, upon release, to interact with the local cell population. The proportion of polymer or co-polymer to protein suitable for the purpose of the present invention will range from about 10% by weight to about 90% by weight of polymer to about 90% to 10% by weight of protein. The preferred amount of protein is from about 20% to about 60% by weight, formulated with sufficient polymer matrix to give 100 parts by weight of the composition.

The mixture of protein and polymer is then molded to form delivery vehicles, which can be shaped in a wide variety of shapes, sizes and forms for delivering the selected bioactive factors to the environment of use. For example, the composition can be shaped as buccal and oral devices or articles, vaginal and intrauterine devices or articles, or intramuscular devices of cylinderical, bullet, elliptical, circular, disk or other shape that is appropriate for placement in the physiological environments.

Other articles made according to the invention include implants, prostheses or artificial glands for dispensing a water-soluble bioactive factor to a local cell population. In this embodiment, the polymer matrix acts as a support for the surrounding bone, or cartilage tissue.

The composition of the present invention can be formulated for delivering a soluble, bioactive factor to a local cell population to produce the desired localized effect. The composition can be used in animals, including warm-blooded animals, humans, primates, farm and sport animals, laboratory animals, reptiles and amphibians. The amount of bioactive factor is, in one embodiment, the amount necessary to affect the local cell population, or an excess of that amount. Generally, the article can contain from about 5 mg to about 30 mg of protein.

The articles made from the composition of the present invention can be manufactured by standard techniques, such as casting or compression molding. Other methods of shaping polymeric materials into articles having the desired size and shape are well known. In one embodiment of the present invention, the dried polymer is blended with the protein in the desired proportion, and the mixture is pressed into circular disks by compression molding. Compression-molded articles can then be further sectioned into pieces having the desired dimensions.

Polyanhydrides have demonstrated the characteristics necessary for a successful delivery vehicle of osteogenic factors. They released the inductive protein(s) at an effective dose over a time period coincident with the accumulation of host target cells, as evidenced by the appearance of cartilage and/or bone at the ectopic site. In addition, there was rapid ingrowth of host tissue to promote direct interaction of bioactive factors with the target cells. The polymers are biocompatible, and the composition is biodegradable so that it will ultimately be resorbed.

It should be emphasized that the water-soluble proteins for use in the present invention although capable of inducing a biological effect in vitro do not induce an effect when implanted alone into the physiological site. Similiarly, the polymers themselves do not induce an effect when implanted alone. Only the combination of water-soluble proteins and polymer was effective.

Polyanhydride polymers have now been shown capable of delivering bioactive factors which act on local cell populations. In addition to chondro/osteogenic factors, bioactive factors such as TGF-beta, EGF, FGF, and PDGF which act upon local cell populations in wound healing or angiogenesis, can be used in the present devices.

The invention is further illustrated by the following exemplification.

EXEMPLIFICATION

Materials and Methods

Preparation of Water-soluble Proteins from Bone Matrix

Water-soluble proteins were prepared from a 4M guanidine hydrochloride extract of demineralized bovine cortical bone as described by Syftestad et al. Syftestad et al., *Differentiation*, 29: 230–237 (1985). Briefly, mid-shaft femoral cortices of 1 year old steers were cleaned of adhering tissue and marrow, decalcified in 0.6N HCl at 4° C., defatted in chloroform:methanol (1:1 v/v) and air dried. The bone matrix was extracted at 4° C. in a solution of 4M guanidine hydrochloride buffered with 50 mM Tris, pH 6.8, and containing enzyme inhibitors. The extract was dialyzed at 4° C. sequentially against solutions of decreasing ionic strength: 0.5M guanidine hydrochloride, 50 mM Tris buffered saline, and distilled water. Precipitates which formed at each step were removed by centrifugation until only those proteins soluble in cold distilled water remained. This portion of the extract was lyophilized and will hereafter be referred to as water-soluble proteins.

Preparation of Polyanhydride Polymers

Poly[bis(p-carboxyphenoxy)propane anhydride] (PCPP) and Poly[bis(p-carboxy)methane anhydride] (PCPM) were synthesized by melt polycondensation. Conix, *Macro. Synth.*, 2: 95–98 (1966); Leong et al., *J. Biomed. Mat. Res.*, 19: 941–955 (1985). Briefly, the dicarboxylic acid monomers were converted to the mixed anhydride by total reflux in acetic anhydride followed by recrystallization. The prepolymers were then subjected to melt polycondensation in vacuo under nitrogen sweep. Copolymers of PCPP and sebacic acid (SA) were obtained in a similar manner. The polymers were purified by extraction with anhydrous ether in a Soxhlet Extractor for several hours and were stored in a desicator over calcium chloride.

Matrices incorporating water-soluble protein were formulated by compression molding. The polymers were ground in a Micro Mill Grinder and sieved into a particle size range of 90–150 µm. Twenty mg of water-soluble proteins were manually mixed with the polymer at the desired ratios (w/w) and the mixture pressed into circular discs in a Carver Test Cylinder Outfit at 30 Kpsi and room temperature. The dimensions of the devices were 14 mm in diameter and 0.9 to 1.1 mm thick. They were manually sectioned into 1 mm$^3$ disks immediately prior to implantation.

In Vivo Assay

Under Metophane anaesthesia, a 1 cm incision was made in the dorsal thigh of 5–7 week old CBA/J mice. The implants were placed between muscle beds, care being taken to avoid contact with the femur. The wound was sealed by clips and swabbed with alcohol. The animals were monitored for signs of inflammation or obvious discomfort, at which time the animal was euthanized and the implant discarded. NIH guidelines for the care and use of laboratory animals (NIH Publication #85-23 Rev. 1985) were observed. The healthy samples were removed 9 or 16 days post-implantation fixed in Perfix (Fisher Scientific), decalcified (if necessary), and processed for histology. Alternate paraffin-embedded sections 5–6 µm thick were stained with either Toluidine blue or Mallory-Heidenhain's stain.

Cartilage was identified by its typical morphology of round cells embedded in an extensive extracellular matrix and by the characteristic metachromatic staining of the extracellular matrix with Toluidine blue. Bone was identified by its characteristic morphology of lining osteoblasts, multinucleated osteoclasts, and osteocytes embedded osteoid and by the dark blue staining of the osteoid with Mallory-Heidenhain's stain. No attempt was made to quantitate the amount of cartilage and/or bone present.

RESULTS

The water-soluble protein preparation from bovine bone matrix used in this study has been previously shown to consist of numerous Coomassie Blue stained protein bands ranging in size from 10 Kd to 100 Kd when subjected to SDS-PAGE. Syftestad et al., *Differentiation*, 29: 230–237 (1985). The water-soluble proteins are capable of inducing chondrogenesis in two in vitro assay systems: the stage 24 chick limb bud system (Syftestad and Caplan, *Dev. Biol.*, 104: 348–356 (1984); Syftestad et al., *Differentiation*, 29: 230–237 (1985)), and day 11 chich embryonic minced muscle explants. Lucas et al., *Differentiation*, 37: 47–52 (1987). When properly formatted in a controlled-release device of the present invention, this protein mixture can also induce ectopic endochondral ossification in the muscle of CBA/J mice. When 20 mg of lyophilized water-soluble proteins were implanted alone into a mouse thigh muscle, however, no signs of cartilage or bone formulation could be detected. Nine days after implantation a "nodule" of connective tissue composed of fibroblastic cell types embedded in a loose extracellular matrix was present. This response is most probably due to the normal wound healing response and was not directly initiated by the implanted water-soluble proteins. By 16 days post-implantation, this connective tissue infiltrate has disappeared making it impossible to locate the original implant site.

Implantation of the polymers, PCPP-SA copolymer, PCPP, or PCPM, alone without the addition of water-soluble proteins also resulted in the accumulation of connective tissue composed of fibroblastic cells as described above. At 9 days post-implantation, polymer and connective tissue cells were visible for PCPP, and PCPP-SA. The connective tissue was unchanged at 16 days post-implantation. None of the polymer implants alone exhibited any formation of cartilage and/or bone (Table 1).

TABLE 1

| Vehicle | Amount of Water-soluble Protein | Number of Implants with Cartilage or Bone/ Number of Implants |
| --- | --- | --- |
| Water-soluble proteins | 20 mg | 0/8 |
| PCPP-SA 30:70 | 0 mg | 0/6 |
| PCPP-SA 30:70 | | |
| 20% loading | 20 mg | 0/4 |
| 30% loading | 20 mg | 0/4 |
| 40% loading | 20 mg | 0/4 |
| PCPP | 0 mg | 0/6 |
| PCPP | | |
| 20% loading | 20 mg | 0/4 |
| 40% loading | 20 mg | 0/4 |
| 60% loading | 20 mg | 3/10 |
| PCPM | 0 mg | 0/6 |
| PCPM | | |
| 20% loading | 20 mg | 0/4 |
| 30% loading | 20 mg | 6/12 |
| 40% loading | 20 mg | 0/4 |
| 50% loading | 20 mg | 0/4 |

When water-soluble proteins were incorporated into PCPP-SA copolymers (ratio of PCPP:SA was 30:70) with 20% loading of protein, the result was the accumulation of connective tissue and inflammatory cells 9 days post-implantation. There was no observable cartilage and/or bone in any of the implants (Table 1). Increasing the loading of protein to 30 and 40% did not result in the induction of cartilage and/or bone (Table 1).

PCPP was tested at protein loadings of 20% and 40%. At these loadings, the implants exhibited connective tissue 9 days post-implantation and were essentially indistinguishable from controls. No cartilage and/or bone was induced (Table 1). However, when the loading was increased to 60%, cartilage was observed at 9 days post-implantation and bone at 16 days post-implantation. The induced cartilage and bone was formed adjacent to the pieces of polymer. The incidence of osteogenesis in the implants was 30%.

PCPM was tested at a variety of loading with water-soluble proteins: 20, 30, 40 and 50%. Only the implants loaded with 30% protein exhibited cartilage and/or bone induction (Table 1). The others contained connective tissue and were essentially identical to implants of PCPM alone. However, at 40% loading, cartilage was observed at day 9 post-implantation. The nodules of cartilage were being invaded by vaculature and the beginning of osteogenesis was observable. The nodules of cartilage and bone were usually formed adjacent to the particles of polymer, but occasionally small particles of polymer could be discerned within the nodule of cartilage. By 16 days post-implantation the cartilage had been replaced by a nodule of trabecular bone. The incidence of induction of cartilage and/or bone in the implants was 50% (Table 1).

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of inducing chondrogenesis and osteogenesis in an animal comprising implanting in the animal a delivery device comprising:

a. a shaped matrix sized and adapted for administration of the bioactive substance to an animal and formed of a polymer selected from the group consisting of polyanhydride and polyorthoester; and b. a therapeutically effective amount of a bioactive substance selected from the group consisting of water soluble chondrogenic or osteogenic proteins derived from demineralized bone matrix, TGF-beta, EGF, FGF and PDGF, wherein the bioactive substance is present in an amount of between about 10 and 90 percent by weight of matrix;

wherein the composition erodes at a controlled rate over a period of time, thereby administering the bioactive substance to the animal in an amount effective to induce formation of cartilage and bone or wound healing.

2. The method of claim 1 wherein the polyanhydride is selected from the group consisting of:

poly[bis(p-carboxyphenoxy)propane anhydride], poly[bis (p-carboxy)methane anhydride] and poly[bis)p-carboxyphenoxy)propane anhydride]-sebacid acid copolymer.

3. The method of claim 1 wherein the water soluble chondrogenic or osteogenic proteins derived from demineralized bone matrix is a mixture of cold water-soluble proteins.

4. The method of claim 3 wherein the cold water-soluble proteins are proteins derived from demineralized bone matrix.

5. The method of claim 1 wherein the chondrogenic or osteogenic proteins is derived from demineralized bovine femur bone matrix.

6. The method of claim 1 wherein the bioactive substance is selected from the group consisting of TGF-beta, EGF, FGF and PDGF.

7. The method of claim 1 wherein the composition comprises a continuous matrix having a bioactive substance interspersed therethrough.

8. The method of claim 1 which is administered to release bioactive substance intramuscularly.

9. The method of claim 1 wherein the shaped matrix sized and adapted for administration of the cartilage and bone inducing substance is formed from a polyanhydride polymer selected from the group consisting of poly(bis(p-carboxyphenoxy)propane anhydride), poly(bis(p-carboxyphenoxy)methane anhydride) and poly(bis(p-carboxyphenoxy)propane anhydride-sebacic acid); and the cartilage and bone inducing amount of a protein preparation derived from demineralized bone matrix consists of a mixture of cold water-soluble proteins capable of inducing chondrogenesis and osteogenesis having a range of molecular weight of from about 10 to about 100 Kd.

* * * * *